United States Patent
Von Pechmann et al.

(10) Patent No.: US 8,840,077 B2
(45) Date of Patent: Sep. 23, 2014

(54) TABLE-MOUNTED SURGICAL INSTRUMENT STABILIZERS

(75) Inventors: Walter Von Pechmann, Bethesda, MD (US); Samuel C. Yoon, Clarksville, MD (US); Ben Lane, Phoenix, MD (US); Keith Lipford, Baltimore, MD (US); Brian Lipford, Bel Air, MD (US)

(73) Assignee: CooperSurgical, Inc., Trumbull, CT (US)

( * ) Notice: Subject to any disclaimer, the term of this patent is extended or adjusted under 35 U.S.C. 154(b) by 239 days.

(21) Appl. No.: 13/589,439

(22) Filed: Aug. 20, 2012

(65) Prior Publication Data

US 2013/0048818 A1 Feb. 28, 2013

Related U.S. Application Data

(60) Provisional application No. 61/526,903, filed on Aug. 24, 2011.

(51) Int. Cl.
 *A61B 17/00* (2006.01)
 *F16M 11/40* (2006.01)
 *A61B 19/00* (2006.01)

(52) U.S. Cl.
 CPC ......... *F16M 11/40* (2013.01); *F16M 2200/022* (2013.01); *A61B 19/26* (2013.01); *A61B 2019/268* (2013.01)
 USPC ..................................... 248/288.31; 600/210

(58) Field of Classification Search
 USPC .......... 248/288.31, 288.51, 160; 403/90, 114, 403/56, 57; 600/210, 229, 230; 606/130, 606/601

See application file for complete search history.

(56) References Cited

U.S. PATENT DOCUMENTS

| | | | |
|---|---|---|---|
| 1,276,117 A * | 8/1918 | Riebe | 464/171 |
| 3,858,578 A | 1/1975 | Milo | |
| 4,143,652 A | 3/1979 | Meier et al. | |
| 4,254,763 A | 3/1981 | McCready et al. | |
| 4,424,724 A | 1/1984 | Bookwalter et al. | |
| 4,767,231 A | 8/1988 | Wallis | |
| 4,775,362 A | 10/1988 | Kronner | |

(Continued)

FOREIGN PATENT DOCUMENTS

| WO | WO 2006/040466 | 4/2006 |
|---|---|---|
| WO | WO 2009/078953 | 6/2009 |

OTHER PUBLICATIONS

U.S. Appl. No. 61/005,746, filed Dec. 7, 2007; entitled : Endoscopic mesh delivery system with integral mesh stabilizer and vaginal probe; pp. 1-33.

(Continued)

*Primary Examiner* — Steven Marsh
(74) *Attorney, Agent, or Firm* — Fish & Richardson P.C.

(57) ABSTRACT

A surgical instrument stabilizer system that includes an articulating boom that is releasably connectable to a surgical table side rail. The articulating boom includes an actuator, a multi-directional flexible arm having a first end region attached to the actuator, and a cable extending through the flexible arm. The cable has one end region connected to the actuator and another end region connected to a preload tensioning mechanism. The actuator is operable to tighten and loosen the cable, and the preload tensioning mechanism maintains an amount of tension in the cable when the actuator loosens the cable. The system further includes a surgical instrument-supporting member that is attached to a second end region of the flexible arm and is configured to releasably retain a surgical instrument.

21 Claims, 6 Drawing Sheets

(56) References Cited

U.S. PATENT DOCUMENTS

| | | |
|---|---|---|
| 4,924,851 A | 5/1990 | Ognier et al. |
| 4,963,903 A | 10/1990 | Cane |
| 5,047,036 A | 9/1991 | Koutrouvelis |
| 5,170,790 A | 12/1992 | Lacoste et al. |
| 5,178,606 A | 1/1993 | Ognier et al. |
| 5,184,601 A | 2/1993 | Putnam |
| 5,351,676 A | 10/1994 | Putnam |
| 5,375,481 A | 12/1994 | Cabreraa et al. |
| 5,383,888 A | 1/1995 | Zvenyatsky et al. |
| 5,409,496 A | 4/1995 | Rowden et al. |
| 5,445,643 A | 8/1995 | Valtchev |
| 5,487,377 A | 1/1996 | Smith et al. |
| 5,520,608 A | 5/1996 | Cabrera et al. |
| 5,520,698 A | 5/1996 | Koh |
| 5,540,700 A | 7/1996 | Rowden et al. |
| 5,554,160 A | 9/1996 | Caillouette |
| 5,556,401 A | 9/1996 | Caillouette |
| 5,560,577 A | 10/1996 | Keselman |
| 5,582,379 A | 12/1996 | Keselman et al. |
| 5,613,926 A * | 3/1997 | Michaelson ............... 482/121 |
| 5,643,285 A | 7/1997 | Rowden et al. |
| 5,643,311 A | 7/1997 | Smith et al. |
| 5,681,325 A | 10/1997 | Hasson |
| 5,782,859 A | 7/1998 | Nicholas |
| 5,800,381 A | 9/1998 | Ognier |
| 5,802,641 A | 9/1998 | Van Steenburg |
| 5,810,806 A | 9/1998 | Ritchart et al. |
| 5,840,077 A | 11/1998 | Rowden |
| 5,918,844 A | 7/1999 | Ognier |
| 6,062,829 A | 5/2000 | Ognier |
| 6,080,118 A | 6/2000 | Blythe |
| 6,096,956 A | 8/2000 | Hoshino |
| 6,235,037 B1 | 5/2001 | East et al. |
| 6,248,101 B1 | 6/2001 | Whitmore et al. |
| 6,328,729 B1 | 12/2001 | Jervis |
| 6,348,036 B1 | 2/2002 | Looney et al. |
| 6,464,630 B1 | 10/2002 | Borst et al. |
| 6,488,030 B1 | 12/2002 | Wardle et al. |
| 6,506,149 B2 | 1/2003 | Peng et al. |
| 6,514,239 B2 | 2/2003 | Shimmura et al. |
| 6,653,055 B1 | 11/2003 | Meier et al. |
| 6,699,235 B2 | 3/2004 | Wallace et al. |
| 6,716,163 B2 | 4/2004 | Muhanna |
| 6,730,020 B2 | 5/2004 | Peng et al. |
| 6,741,895 B1 | 5/2004 | Gafni et al. |
| 6,758,809 B2 * | 7/2004 | Briscoe et al. ............ 600/229 |
| 6,860,668 B2 * | 3/2005 | Ibrahim et al. ................ 403/56 |
| 6,884,212 B2 | 4/2005 | Thierfelder et al. |
| 6,932,759 B2 | 8/2005 | Kammerer et al. |
| 6,949,105 B2 | 9/2005 | Bryan et al. |
| 6,958,038 B2 | 10/2005 | Feng et al. |
| 7,052,453 B2 | 5/2006 | Prethus et al. |
| 7,066,926 B2 | 6/2006 | Wallace et al. |
| 7,125,380 B2 | 10/2006 | Yager |
| 7,131,944 B2 | 11/2006 | Jacquetin |
| 7,156,806 B2 | 1/2007 | Dobrovolny |
| 7,189,246 B2 | 3/2007 | Otsuka et al. |
| 7,223,229 B2 | 5/2007 | Inman et al. |
| 7,311,664 B2 * | 12/2007 | Goodman et al. ............ 600/228 |
| 7,347,812 B2 | 3/2008 | Mellier |
| 7,517,313 B2 | 4/2009 | Thierfelder et al. |
| 7,634,874 B2 * | 12/2009 | Lucas ............................ 52/108 |
| 7,867,161 B2 | 1/2011 | Staskin et al. |
| 2003/0195386 A1 | 10/2003 | Thierfelder et al. |
| 2003/0220538 A1 | 11/2003 | Jacquetin |
| 2004/0172012 A1 | 9/2004 | Otsuka et al. |
| 2004/0230092 A1 | 11/2004 | Thierfelder et al. |
| 2005/0065395 A1 | 3/2005 | Mellier |
| 2006/0015001 A1 | 1/2006 | Staskin et al. |
| 2006/0199994 A1 | 9/2006 | Inman et al. |
| 2007/0073493 A1 | 3/2007 | Ognier |
| 2007/0129615 A1 | 6/2007 | Backman et al. |
| 2007/0129634 A1 | 6/2007 | Hickey et al. |
| 2008/0221590 A1 | 9/2008 | Ikeda et al. |
| 2009/0072107 A1 * | 3/2009 | Wilson et al. ............... 248/279.1 |
| 2010/0160928 A1 | 6/2010 | Navas et al. |
| 2010/0280309 A1 | 11/2010 | von Pechmann |

OTHER PUBLICATIONS

CooperSurgical, Uterine Positioning Syustem, Brochure pp. 1-5; Form #81464; Rev. Dec. 2008.

Culligan et al., "Long-Term Success of Abdominal Sacral Colpopexy Using Sunthetic Mesh," *Am. J. obstet. Gynecol.*, Dec. 2002.

Endoboy Pneumatic Manipulator Arm Instruction Manual; Dec. 7, 2002; Geyser s.a.; France; pp. 1-21.

Magrina vaginal retractor as illustrated in the catalog entitled: "Bookwaltre Retractor System," pp. 1-48; Feb. 25, 2008.

Martin's Arm (LTL Medical, LLC) as illustrated on the website: http://www.ltlmedical.net/martins-arm.html. Last visited Feb. 9, 2011; 1 page.

* cited by examiner

TABLE-MOUNTED SURGICAL INSTRUMENT STABILIZERS

CROSS-REFERENCE TO RELATED APPLICATIONS

This application claims the benefit of U.S. Application Ser. No. 61/526,903, filed on Aug. 24, 2011, which is incorporated by reference herein.

TECHNICAL FIELD

This invention relates to table-mounted surgical instrument stabilizers.

BACKGROUND

During surgery, whether open or laparoscopic, there is a need for a device that can be utilized to stabilize surgical instruments for various functions, most commonly for stabilizing instruments that would otherwise be handheld, in order to achieve desired tissue tension or to maintain exposure to the surgical site. Many such apparatuses already exist.

SUMMARY

In one aspect of the invention, a surgical instrument stabilizer system includes an articulating boom that is releasably connectable to a surgical table side rail. The articulating boom includes an actuator, a multi-directional flexible arm having a first end region attached to the actuator, and a cable extending through the flexible arm. The cable has one end region connected to the actuator and another end region connected to a preload tensioning mechanism. The actuator is operable to tighten and loosen the cable, and the preload tensioning mechanism maintains an amount of tension in the cable when the actuator loosens the cable. The system further includes a surgical instrument-supporting member attached to a second end region of the flexible arm. The surgical instrument is configured to releasably retain a surgical instrument.

Embodiments can include one or more of the following features.

In some embodiments, the flexible arm includes a plurality of nesting links, each of which has a hemispherical end region and a concave end region. The hemispherical end regions of the nesting links matingly engage the concave end regions of adjacent nesting links such that the nesting links are movable relative to one another.

In certain embodiments, a maximum diameter of the concave end region of one of the nesting links is smaller than a maximum outer diameter of the hemispherical end region of another one of the nesting links that is mated with the concave end region of the one of the nesting links.

In some embodiments, average diameters of the nesting links progressively decrease in the direction of the surgical instrument-supporting member.

In certain embodiments, each of the plurality of nesting links has an internal tubular member and an outer wall that concentrically surrounds the internal tubular member, and the internal tubular member of each of the nesting links defines a lumen for passage of the cable.

In some embodiments, the outer wall defines the concave end region in each of the nesting links.

In certain embodiments, the internal tubular member of each of the nesting links extends axially beyond the outer wall.

In some embodiments, the internal tubular member of each of the nesting links has a bottleneck configuration.

In certain embodiments, a first portion of the lumen extending along the concave end region of each of the nesting links has a smaller diameter than a second portion of the lumen extending along the hemispherical end region of each of the nesting links.

In some embodiments, the second portion of the lumen of each of the nesting links receives therein a portion of the tubular member of an adjacent one of the nesting links.

In certain embodiments, the lumen and the tubular member of each of the nesting links are configured such that contact between the inner and outer walls, respectively, of adjacent nesting links limits rotations of the adjacent nesting links relative to one another.

In some embodiments, a contact angle at which a compressive force of one of the nesting links contacts an adjacent one of the nesting links is 18-30 degrees.

In certain embodiments, the lumen of each of the nesting links has a first end, a central region, and a second end, and the lumen decreases in diameter from the first end to the central region and increases in diameter from the central region to the second end.

In some embodiments, the internal members of the nesting links are shaped to maintain the cable centered within each of the nesting links when the flexible arm is bent into a non-linear configuration.

In certain embodiments, the surgical instrument stabilizer system further includes an elastic grommet disposed within the lumen of each of the nesting links.

In some embodiments, the preload tensioning mechanism includes a compression spring mounted on an anchor that is attached to the cable.

In certain embodiments, the anchor includes a bulbous head, and the compression spring is mounted between the bulbous head of the anchor and a surface of the surgical instrument-supporting member.

In some embodiments, the compression spring is biased to move the anchor and the cable away from the surface of the surgical instrument-supporting member.

In certain embodiments, the surgical instrument-supporting member includes a collar, and the surface of the surgical instrument-supporting member is an internal surface of the collar.

In some embodiments, the collar is configured to permit rotation of the surgical instrument-supporting member relative to the flexible arm.

In certain embodiments, the surgical instrument stabilizer system further includes a rigid arm assembly that supports the articulating boom and that is attached to a side rail of a surgical table by a clamping assembly in a manner such that the rigid arm assembly and the articulating boom can be slid along the side rail.

In some embodiments, the surgical instrument stabilizer system further includes a locking ball coupling that connects the rigid arm assembly to the articulating boom, and the locking ball coupling carries the articulating boom at the center of gravity of the articulating boom.

In certain embodiments, the surgical instrument stabilizer system further includes a surgical instrument that is secured in the instrument-supporting member and can be repositioned and locked in a desired position and orientation single-handedly.

Embodiments can include one or more of the following advantages.

In some embodiments, the stabilizer system serves to securely hold any of various different instruments during any of various different procedures, for example, during laparoscopic sacral colpopexy which requires a stable probe during suturing of mesh to the vagina. The system is portable and may be attached anywhere around the opposing side-rails and/or head/foot rails mounted along an existing surgical table to provide a combination of different adjustment capabilities, effectively allowing a surgeon to manually position and then stabilize an instrument anywhere above and around the table at any orientation, on demand. In some cases, the instrument can be operated using only one hand or by voice activation.

In certain embodiments, a first range of unidirectional positioning is achieved with a flexible arm connected to an instrument-supporting hand piece, the arm allowing the handpiece to be positioned anywhere and at any orientation within reach of the arm, and the arm "frozen" to lock the instrument in that position. A second range of unidirectional positioning is achieved by mounting the flexible arm in an articulating base that includes a locking ball joint. The arm may be reoriented anywhere within a hemispherical range of motion about ball joint and locked in position. Moreover, the articulating base is suspended from a clamping assembly that may be clamped to the rails of a conventional surgical table anywhere around the table. Consequently, a third range of unidirectional positioning is achieved by translating the clamping assembly around the table. Lastly, a fourth range of motion is achieved by the instrument-supporting hand piece (at the end of the flexible arm), which is pivotal for angular orientation of the instrument supported thereby.

Thus, in some embodiments, the system allows easy single handed (or voice activated) repositioning in multiple directions (any direction, rotation or angle) when in an "unlocked" condition, a secure fixed position when in a "locked" condition, and with variable user-adjustable resistance there between, coupled with same hand (or voice activated) control over the rigidity of the flexible arm combined with the delivery of vacuum when applicable.

In certain implementations, the flexible arm of the systems is configured to minimize or eliminate hand piece shifting or drift, and improve the stability of a surgical instrument (e.g., vaginal probe) being supported thereby.

DETAILED DESCRIPTION

Figure 1:
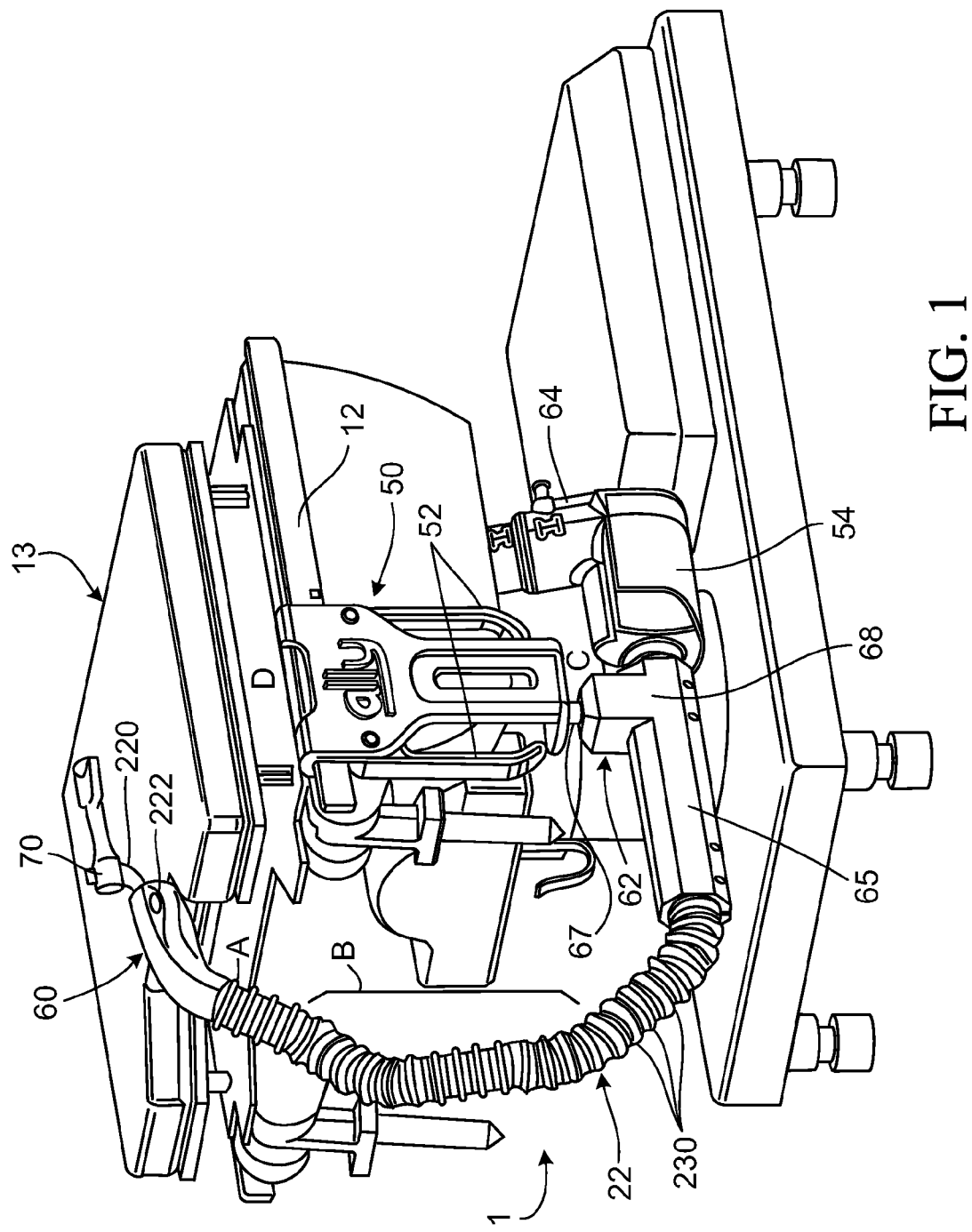
FIG. 1 is a perspective view of an exemplary embodiment of a stabilizer system.

FIG. 1 is a side perspective view of an exemplary embodiment of the stabilizer system 1. The stabilizer system 1 is portable and attaches to the existing horizontal side and end-rails 12 mounted to the opposing sides and ends of most surgical tables 13. The rails 12 are typically mounted on spacers so as to space them approximately 1" outward from the table 13. Many surgical tables in the United States employ standardized North American rails, which are well suited for present purposes. A quick-release clamping assembly 50 can be attached anywhere along the rails 12 for supporting the entire stabilizer system 1 therefrom. The quick-release clamping assembly 50 hooks overtop the rail 12 and clamps via a pair of lever arms 52 that bear against the bottom of the rail 12, allowing them to manually clamp assembly 50 about the rail 12 for supporting the entire stabilizer system 1 therefrom. The quick-release clamping assembly 50 suspends a ball coupling 67 including a short link having a ball at the distal end. The ball of coupling 67 is pivotally inserted into a base 65, and specifically into a locking receptacle 68 of base 65 thereby forming a first locking ball-and-socket pivot joint. The other end of ball coupling 67 may be fixedly secured to quick-release clamping assembly 50, as shown in FIG. 1, or as shown below with reference to FIG. 2, may be pivotally attached to quick-release clamping assembly 50 by a second locking ball-and-socket pivot joint. The base 65 carries an articulating boom including an actuator 64 mounted inside actuator housing 54. The actuator housing 54 may be integral to base 65 as shown and contains a servo motor or other suitable actuator. Base 65 extends to a flexible arm 22 mounted thereto. The ball coupling 67 suspends the entire articulating boom at any desired orientation within a hemispherical range of motion vis a vis the orientation of its ball inside the locking receptacle 68 of base 65, and the orientation of ball coupling 67 may be adjusted by unlocking receptacle 68 of base 65, adjusting, and then clamping it in place again.

Figure 2:
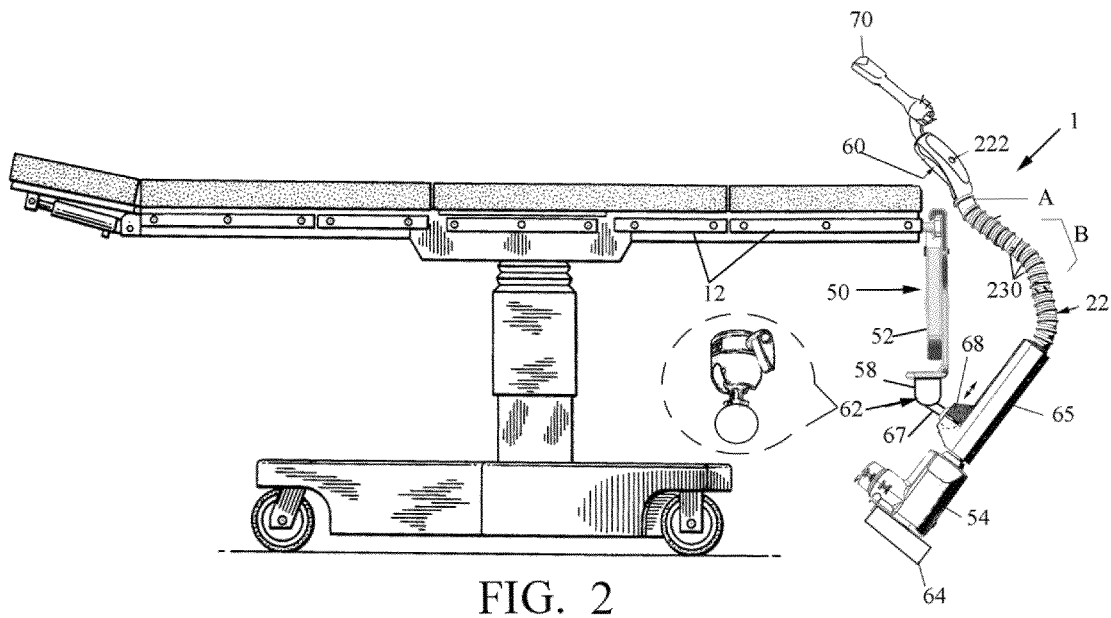
FIG. 2 is a side view of another embodiment of a stabilizer system similar to FIG. 1 with an additional (optional) ball joint.

FIG. 2 is a side view of a similar embodiment of the stabilizer system 1. In this embodiment, the stabilizer system 1 includes an additional (optional) ball joint 62 beneath the clamping assembly 50. The quick-release clamping assembly 50 suspends the ball-hitch mechanism 62 downward from the rail 12. The ball-hitch mechanism 62 includes a locking ball-in-socket receptacle 58 fixedly attached to the quick-release clamping assembly 50, and a dogbone ball coupling 67 including a short link having a ball coupling at both ends. One end of dogbone ball coupling 67 is pivotally inserted into the ball-hitch mechanism 54 thereby forming a first locking ball-and-socket pivot joint. The other end of dogbone ball coupling 67 is pivotally clamped in a base 65 thereby forming a second locking ball-and-socket pivot joint. The ball coupling 67 can at any of various different orientations from the ball-hitch mechanism 62 into a locking receptacle 68 of base 65, and the orientation of ball coupling 67 may be adjusted within a hemispherical range of motion by unlocking ball-in-socket receptacle 58, adjusting, and then clamping it in place again. The ball-hitch mechanism 62 is essentially a heavy-duty camera tripod head as shown in the inset of FIG. 2, with a manual lock-screw.

In operation, the locking receptacle 68 of base 65 provides the entire articulating boom with unidirectional positioning capability around a large number of different axes, and the (optional) suspended ball-hitch mechanism 62 of FIG. 2 extends the range of motion. In effect, the clamping assembly 50 may be clamped anywhere around the rails 12 of conventional surgical table 13, thereby providing a first range of positioning around a horizontal rectangular plane. A second range of unidirectional positioning is achieved by suspending the boom and flexible arm 22 from a fulcrum at the ball coupling 67 (and at ball-hitch mechanism 62 if included). The arm 22 may be reoriented anywhere within a hemispherical range of motion and locked in position.

Figure 3:
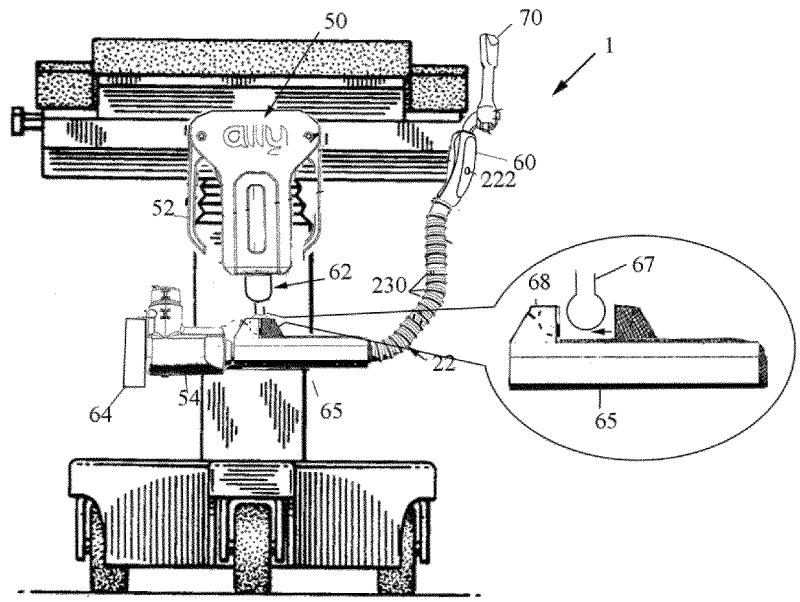
FIG. 3 is an end view of the stabilizer system shown in FIG. 2.

FIG. 3 is an end view of the stabilizer system 1 as in FIG. 2 with an enlarged inset of the locking receptacle 68. The locking receptacle 68 includes two-opposed half-cup-shaped members, one fixed and one translatable along base 65. The ball coupling 67 extends transversely from the clamping assembly 50 into the locking receptacle 68 of base 65, and the cooperating halves of the locking receptacle 68 operate in a vice-like manner to selectively lock/release the ball coupling 67 in position. Drawing the cup-shaped members together clamps the ball coupling 67 in a stationary position, and the mechanism for doing this may be any suitable internal gearing or electric or pneumatic means. Releasing pressure from the cup-shaped members unclamps the ball coupling 67 for free pivoting, but does not initially allow release of the boom. If desired, the failsafe position of the cup-shaped members of the locking receptacle 68 may be further separated for full removal of the boom from the clamping assembly 50.

The ball coupling 67 typically extends into the base 65 at or very near the center of gravity of the entire articulating boom. As a result, when the physician unclamps the locking receptacle 68, the articulating boom does not pivot wildly.

Figure 5:
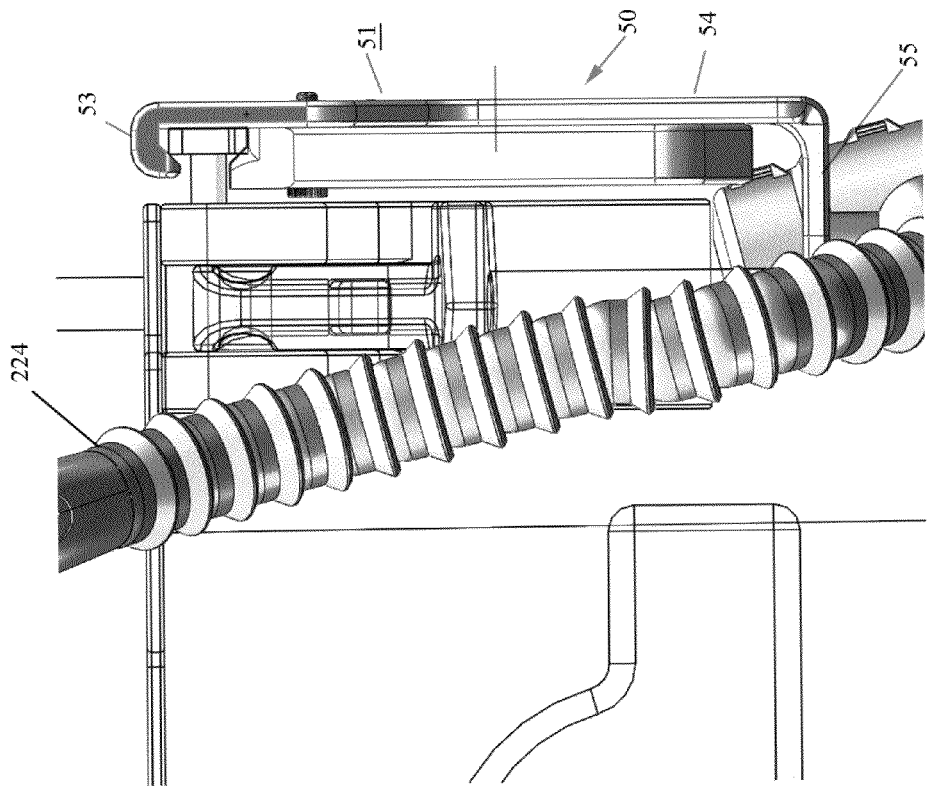
FIG. 5 is a side view of the quick-release clamping assembly of FIG. 4.
Figure 4:
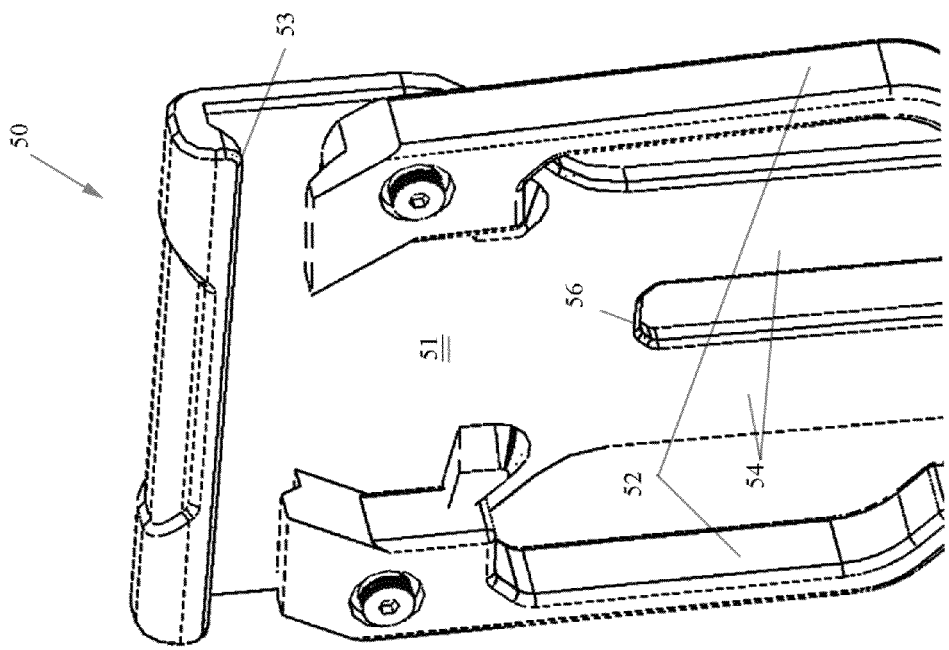
FIG. 4 is a perspective view of a quick-release clamping assembly of the stabilizer systems of FIGS. 1-3.

With reference to FIGS. 4 and 5, the quick-release clamping assembly 50 may be clamped anywhere around the rails of a conventional surgical table. The quick-release clamping assembly 50 includes a plate member 51 that extends upward to a hooked upper edge 53. The hooked upper edge 53 hooks overtop the rail 12 in a tongue-and-groove manner. The lever arms 52 are pivotally mounted to the plate member 51 and when pivoted together to the position shown in FIG. 4, they conform to the rail 12 and bias it tight from beneath, likewise in a tongue-and-groove manner. If desired, roller(s) or pads can be provided along the upper bearing surfaces of lever arms 52 to reduce friction against the side rails 12 when clamping tight. Either way, the lever arms 52 effectively clamp tight to the rail 12, allowing it to support the entire stabilizer system 1. Beneath the lever arms 52 the plate member 51 extends downward to a support member defined as a reverse-L-shaped member having a vertical portion and inwardly-turned horizontal flange 55, and a central notch 56 running a majority of the length of the vertical portion and inwardly-turned horizontal flange 55, bisecting the support member into two opposed sides 54. The ball coupling 67 (or ball-hitch mechanism 62) may be bolted anywhere along the notch 56 to plate member 51, thereby allowing a vertical-downward or horizontal-outward orientation of the ball-hitch mechanism 62.

Referring back to FIG. 1, the flexible arm 22 continues to a hand piece 60 within which a surgical instrument such as a probe 70 is mounted. The flexible arm 22 includes a plurality of mating ball and socket links 230 optionally covered with a thin walled elastomeric sheath (not shown). The sheath is intended to improve sterilization capabilities and improve the aesthetics.

A tensioning cable 240 (described below) runs throughout the arm 22 and base 65 to actuator 64 where it connects thereto by a pulley or other suitable mechanism, the actuator 64 controlling the tension load on the cable 240. As the cable 240 tension is increased, the links 230 endure a corresponding increase in compressive load between each mating ball and socket. This loading system creates normal force loads between the ball and socket links 230, which in turn generates friction loads. As loads on each link 230 are increased (with higher tension in the cable 240), each link 230 imposes higher friction forces, which collectively alters the overall flexibility of the arm 22. Thus, at higher cable 240 tension, the arm 22 will endure external loads such as a surgeon pressing on a given tool (such as probe 70) that is being supported by the system 1. Therefore, greater tension in the cable 240 allows the arm 22 to support higher loads at the end of the arm 22 that supports a given tool, due to the increased friction between the links 230. At low cable 240 tension, there is little friction between the links 230 and the arm 22 can be manually moved and positioned by the operator with little resistance. Thus, the stiffness of the arm 22 and hence the amount of friction between links 230 is important, and this is a function of a number of variables including the geometry of the links 230, materials, mating surface finishes, and the magnitude of the normal force on each link.

It is essential for certain procedures that the arm 22, once locked in position, minimizes or eliminates hand piece 60 drift which can affect the stability of the probe 70 or other instrument being supported thereby. It is also desirable to accomplish the foregoing with minimum cable 240 tension, so as to reduce the necessary power requirements of the tensioning actuator 64. The preferred links 230 accomplish this with a particular geometry, size, materials and surface finish which are described in detail below. The movement of the cable 240 by actuator 64 (and hence the tension in the cable 240) may be controlled in various ways. For example, the tension in the cable can be controlled by a button 222 mounted on the instrument-supporting hand piece 60, which button 222 may be connected to actuator 64 via a hard wired connection, optical, infrared, RF, Bluetooth (or other wireless communication). When used with a hard wired or optical connection, a slip ring or rotating connector collar 224 (see FIG. 5) is preferably incorporated at the base of the hand piece 60 to allow the wires or optical fibers to slip relative to the mating link 230 and therefore prevent damage to the wires or fibers that could occur when the hand piece 60 is over rotated by the operator relative to the actuator 64.

Alternatively, button 222 may be replaced with a foot pedal controller in communication with the actuator 64. Button 222 may also be replaced with a voice activated control system in communication with the actuator 64. A suitable voice activated control system includes a microphone coupled to an audio amplifier in turn coupled to a processor capable of running voice recognition software, such as Dragon Naturally Speaking™ software commercially available from Nuance™, or Fonix FAAST™ software commercially available from Fonix Corporation, 1225 Eagle Gate Tower, 60 East South Temple, Salt Lake City, Utah.

The processor may be the actuator 64 control system. Button 222 (or foot pedal or voice control) provides for convenient same hand (or voice)-operated control over the amount of flex imparted to the arm 22. Pressing the button 222 or foot pedal (and holding it in this orientation), causes the cable 240 in the actuator 64 to extend or grow in length which reduces the amount of tension in the cable 240 by a predetermined amount and thereby reduces the friction load between the links 230 such that the flexible arm 22 can move in a more relaxed manner as chosen by the operator. Releasing the button 222 causes the cable 240 in the actuator 64 to retract in overall length which increases the amount of tension in the cable 240 by a predetermined amount, thereby increasing the friction load between the links 230 such that the flexible arm 22 has increased rigidity to a selectable degree chosen by the operator. At maximum tension the arm 22 becomes fully rigid in that the links 230 will not rotate relative to each other unless the maximum loading of the arm 22 is exceeded.

In the case of voice activation, the operator will be able to control the movement and location of the flexible arm 22 through oral messages interpreted by an on-board processor such as the actuator 64 control system.

Hand piece 60 is an ergonomic instrument-supporting receptacle mounted to the distal end of the flexible arm 22, and the hand piece 60 accepts a variety of probe-adapter inserts 220 each of which serves as a conforming receptacle for insertion of a probe 70 or other instrument. In the illustrated embodiment of FIG. 1, a vaginal probe 70 is mounted in the probe-adapter insert 220 on the instrument-supporting hand piece 60. Although, it should be understood that most any instrument or imaging device may be so mounted with a conforming probe-adapter insert 220.

In some embodiments, the system 1 can: 1) allow easy single handed (or voice control) repositioning of the arm 22 in multiple directions (any direction, rotation or angle) when in an unloaded or "unlocked" condition; 2) provide a secure fixed position when in a "locked" condition; and 3) provide the user with variable user-adjustable resistance there between, coupled with single-hand or voice activated-control over the rigidity of the flexible arm 22. This would be well-suited for situations requiring frequent repositioning, such as for stabilization of a laparoscopic camera, and would be equally suited for stabilizing a rectal probe, uterine manipulator, vaginal probe 70 or similar surgical tools. The need for adjustable resistance arises from the different types of instruments requiring stabilization. For instance, a table mounted stabilizer used to hold a laparoscopic camera in a fixed position requires only minimal resistance because it need only resist the weight of the camera itself. In contrast, a stabilizer used to hold a vaginal probe used during laparoscopic sacral colpopexy or a uterine manipulator during laparoscopic hysterectomy would require substantially greater resistance in order to keep the probe stable during suturing of mesh to the vagina. The present invention accomplishes this by including the ability to adjust the overall tension in the cable 240.

The system provides multiple features for "on-the-fly" adjustment of the location and operating range of the flexible arm 22 via four primary surgeon-effected adjustments settings A thru D as described below (with reference to FIG. 1):

At point A, the instrument-supporting hand piece 60 is pivotally mounted to the distal end of the flexible arm 22 for angular orientation of the instrument supported thereby.

Point B is the omnidirectional adjustment and articulation implemented by the flexible arm 22 for local positioning (controlled by button 222 or foot pedal or voice) with internal tensioning cable 240 (allowing multi-axis positioning by the plurality of ball and socket links 230).

Point C (ball coupling 67 in locking receptacle 68) allows spherical global positioning of both the flexible arm 22 and instrument-supporting hand piece 60. This is accomplished by releasing the locking receptacle 68 to unlock and pivot the ball coupling 67, and relocking.

Finally, Point D allows global lengthwise positioning of the entire boom including flexible arm 22, instrument-supporting hand piece 60, actuator 64, and clamping assembly 50 along the surgical table 13 by virtue of the quick-release clamping assembly 50, which is movably mounted to the side-rails 12. The foregoing configuration facilitates easy local and global multi-directional repositioning of the supported instrument and variable resistance-setting. The range of motion is significantly increased by this combination. Surgical instruments can be supported in any location and any orientation within a 60 centimeter diameter spherical range of the point of origin of the instrument-supporting hand piece 60.

Moreover, as described more fully below, the selection parameters of the material used for the flexible elements 230 (e.g., high modulus of elasticity), combined with manufacturing requirements for controlled and uniform surface finish (e.g., injection molding) as well as the design of the optimum geometry of the flexible elements 230 has enabled the load carrying capacity of the foregoing configuration to be substantially greater than prior art stabilizers.

Figure 6:
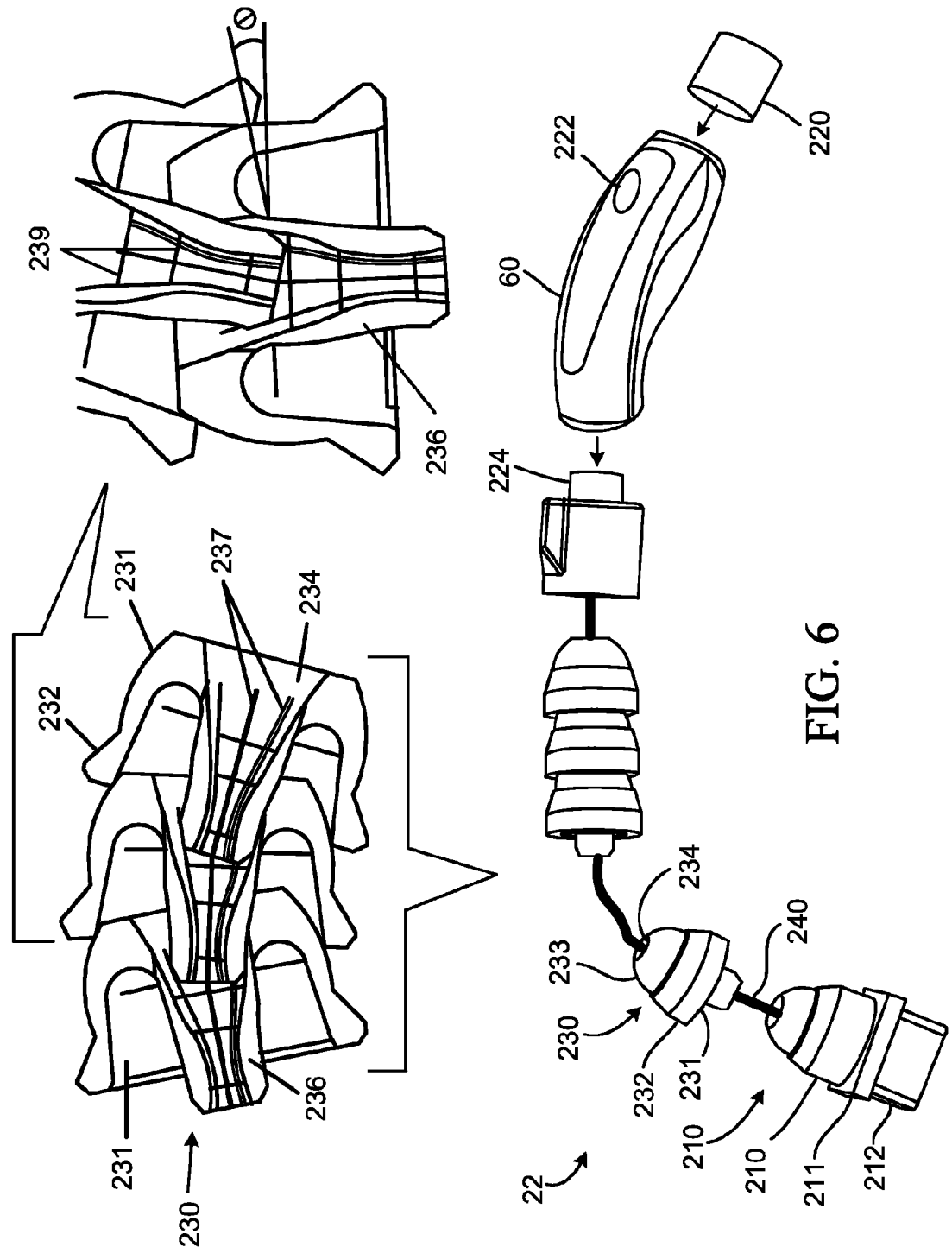
FIG. 6 illustrates a flexible arm used in the stabilizer systems of FIGS. 1-3, with enlarged insets to provide more detailed views of certain features of the flexible arm.

As indicated above, the flexible arm 22 includes a plurality of links 230, optionally covered with a thin walled elastomeric sheath. FIG. 6 illustrates the presently-preferred flexible arm configuration which generally includes an end adapter 210 at one end for insertion into the actuator housing 54, and a hand piece 60 at the other end for mounting the desired surgical tool that needs to be stabilized, a plurality of ball-and-socket links 230 there between, and a tensioning cable 240 anchored in the collar 224 and running throughout the ball-and-socket links 230, end adapter 210 and actuator housing 54, and engaged to the actuator 64 for selectively tensioning or releasing ball-and-socket links 230. The cable 240 is attached at one end to the actuator 64 and at the other end to collar 224 which serves as an anchor for the cable 240 terminus. The ergonomic instrument-supporting hand piece 60 is mounted at the distal end of the flexible arm 22, and the hand piece 60 accepts a variety of surgical tool adapters 220 as described above each of which is fitted to serve as a receptacle for insertion of a surgical tool, such as the vaginal probe 70, a camera, a cutting instrument, etc. If desired (though not shown), ball-and-socket links 230 may be covered with a thin walled elastomeric sheath end-to-end for aesthetics and possible cleaning and sterilization improvement issues. The tensioning cable 240 may be any suitable twisted fiber cord or cable. Typically, ⅛" stainless steel wire rope is used to form the tensioning cable 240. The cable 240 runs throughout the links 230 of the arm 22 and through the actuator housing 54 to the motor pulley (or actuator cylinder) in actuator 64, and in this way the actuator 64 can gradually pull (tension) the cable 240, which compresses the links 230 together to increase their collective rigidity, and ultimately lock them in position. The primary parameters of the flexible arm 22 are its ability to articulate mechanically in any direction, electrically or mechanically freeze a desired position along its entire length, and hold that position with maximum strength and rigidity. The flexible arm 22 typically does this with between 5 and 50 ball-and-socket links 230 configured as shown.

Several design features for these links 230 are described below which were developed to optimize the performance of the system 1. Shifting of the distal end of the arm 22 when placed under load is highly undesirable since the arm must securely hold and position precision surgical tools, cutting instruments, probes and/or cameras. Unexpected shifting can, in certain cases, cause injury to the patient or complications for the user. It is desired for present purposes that the arm 22, once locked in position, minimizes or eliminates hand piece 60 shifting ("drift") which can affect the stability of the probe 70 being supported thereby. It is also desirable to accomplish the foregoing with minimal cable 24 tension, so as to reduce the necessary power of the tensioning drive system. The stiffness of the arm 22 is a function of a number of variables including the geometry of the links 230 (e.g., the size of the links 230), the materials of the links 230, the mating surface finishes, and the magnitude of the normal force on each link. The preferred geometry, size, materials and surface finish of the links 230 for accomplishing this follow.

Materials

The optimal material for links 230 will have a high static and sliding coefficient of friction. Typically, the static frictional coefficient will be in excess of 0.7 and the sliding coefficient of friction will exceed 0.5. Examples of suitable materials include Ultem® PolyEtherlmide ("PEI") which is a high performance polymer with static/sliding coefficients of friction of 0.8, plus excellent dimensional stability combined with chemical resistance, and aluminum which exhibits improved material properties and even higher coefficients of frictions (1.05-1.35 static, 1.4 sliding).

Geometry of Links

As seen in the insets to FIG. 6, the links 230 have a ball-and-socket design, with a convex partial-spheric face or dome 233 at one end and a concave partial-spheric face or recess 231 at the other end. Each convex dome 233 on one link conforms to the concave recess 231 on the adjoining link. The ball-and-socket links 230 nest end-to-end and are capable of limiting relative pivoting. The spherical diameter of the concave end 231 is purposefully designed to be slightly smaller than the mating convex end 233. This concentrates a portion of the reaction load along a circular line formed between the two mating spherical parts. This in turn increases the normal force along a circular line of contact, thereby increasing the friction loads and the moment carrying load capacity of the joint by maintaining an optimal friction loading geometry in each link. Each link 230 typically has a convex partial-spherical face 233 with a maximum diameter of about 1.5 inches, and within a range of from 0.5 to 4 inches, leading to a pronounced bell-shaped lip 232. The concave end 231 is typically sized to be 0.006 inches smaller in diameter than the convex part, although other combinations of material properties and sizes could also be used to achieve some measure of this feature. It is understood that the flexible arm 22 and the boom as a whole should be as lightweight as possible, and so the links 230 are typically as small as possible.

Moreover, when a load is applied to the probe 70, the moment load throughout the flexible neck 22 increases with distance from the applied load. Consequently, the size of the links 230 toward the probe 70 need not be as large as those toward the base 65. Therefore, in some embodiments, the links 230 progressively increase in diameter/weight proximally toward the base 65.

The geometry of the links can ensure that adjacent links 230 contact each other at the appropriate contact angle θ, as shown in FIG. 6 inset (top right). The moment-carrying capability (and hence anti-slip resistance) of the flexible arm 22 is a function of the contact angle Θ, i.e., the angle at which the compressive force of a link 230 contacts the next adjacent link, measured as an offset from horizontal. The moment-carrying capability can be calculated using the following equations.

$$F_N = \frac{T}{\sin(\theta)} \quad \text{Normal force on ball surface}$$

$$F_T = \mu \cdot F_N \quad \text{Tangential force on ball surface}$$

Moment Carrying Capability of Link $$M = 2 \cdot \int_0^\pi \frac{F_T}{2 \cdot \pi} \cdot [R \cdot \sin(\theta) + (R - R \cdot \sin(\theta)) \cdot \sin(\phi)] d\phi$$

$$\phi = \text{angle in hoop direction}$$

$$M = \frac{F_T \cdot R}{\pi} \cdot [2 + (\pi - 2) \cdot \sin(\theta)] = \frac{\mu \cdot F_N \cdot R}{\pi} \cdot [2 + (\pi - 2) \cdot \sin(\theta)]$$

Figure 7:
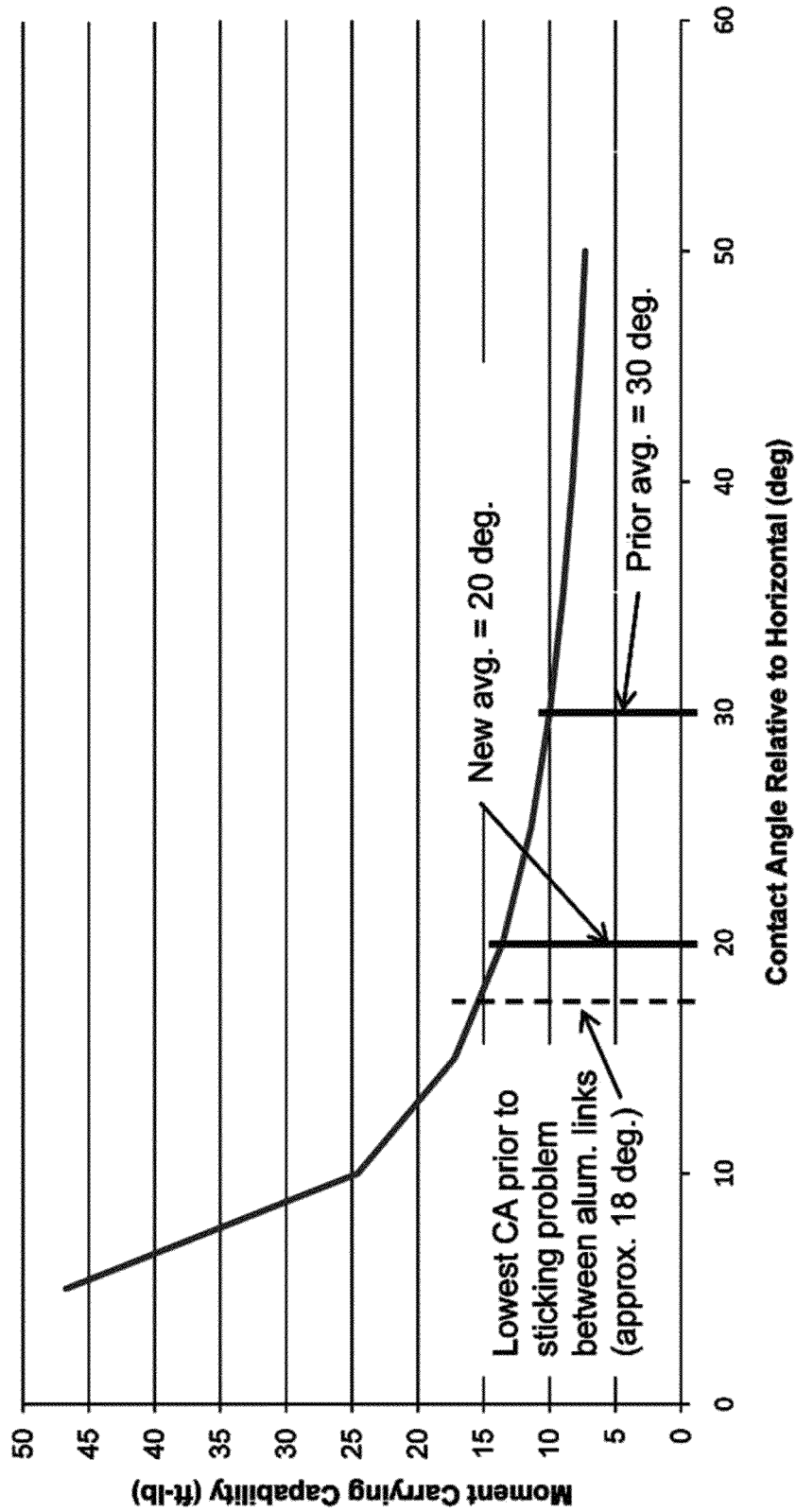
FIG. 7 is a graph of the moment-carrying capability (ft-lbs) of two links of the flexible arm shown in FIG. 6, as a function of a contact angle θ (degrees offset from horizontal).

FIG. 7 is a graph of the moment-carrying capability (ft-lbs) of two links 230 as a function of the contact angle θ (degrees offset from horizontal). As the contact angle θ increases, the moment-carrying capability exponentially decreases, and so the contact angle θ is preferably minimized. On the other hand, if contact angle θ falls below a minimum of approximately 18 degrees for aluminum material, the links 230 are prone to sticking. Applicant's research indicates that optimum contact angle θ is approximately 20 degrees for aluminum, within an acceptable range of from 18-30 degrees. Consequently, each convex dome 233 on one link is dimensioned to conform to the concave recess 231 on the adjoining link accordingly, resulting in an ideal interface orientation between links 230 to maximize holding capacity of the links while minimizing the necessary cable tension load.

The convex partial-spherical face 233 of each link 230 is defined by an aperture 234 for cable 240 passage, and the cable passage continues through the link 230 through a tubular member 236 which traverses the link 230 exiting through the concave end 231 and protruding a short length there beyond. The tubular member 236 nests adjacent links 230 and limits over-rotation of the links 230 while also maintaining concentricity with the cable 240. All three of these can be important factors. Specifically, the tubular member 236 maintains a nested mating relationship between adjacent links 230 and limits over-rotation, thereby ensuring that the plurality of links 230 define a smooth overall curvature (eliminating localized kinks in the arm 22). This ensures smoother operation of the link system when not under actuation load, and prevents individual links 230 from randomly cocking on the cable 240. It has been found that if adjacent links 230 over rotate off their spherical face 233 their behavior becomes unpredictable, and the tubular member 236 prevents this. Moreover, the tubular member 236 as well as the internal geometry of the tubular member 236 act as a cable guide to ensure that the cable 240 maintains a smooth overall curvature inside. If the cable routing is eccentric the flexible arm 22 will kick in a direction upon cable loading. The tubular member 236 guides the cable in close concentricity through the links 230 and maintains a uniform curvature of the cable 240 through links 230. Further toward this end, it can be seen that the internal walls of the tubular member 236 are contoured lengthwise to essentially define a bottleneck, more open at the convex end 233, constricted about two-thirds of the length toward the concave end 231, and opening outward slightly at the concave end 231. The bottleneck configuration of the inner walls of tubular member 236 guide the cable through each link 230 in a uniform arcuate path directly through the center of the links 230, and ensures that the cable 240 maintains the same concentric-curvilinear path from link 230 to link 230. The net result is a uniform cable curvature in close concentricity throughout the entire flexible arm 22, which assures uniform compression of all the links 230 and avoids any preferential compression between any two links 230. Otherwise, given that the cable may experience in excess of 1000 lbs of tension, the configuration described prevents eccentricity which promotes preferential compression on one side or other, thereby avoiding movement, kicking or shifting of the arm 22 to one side.

In practice, the cable terminus will typically be equipped with a swage fitting that is inserted through the links 230 during manufacturing, and this constraint compels a slightly larger lumen through the tubular members 236 to accommodate the swage fitting. This would otherwise detract from the need for close concentricity of the cable and could promote preferential forces, rubbing and abrasion. To alleviate this, it is envisioned that the interior walls of the tubular members 236 may include a flexible (rubberized) grommet-like insert that expands to allow for passage of the cable swage fitting (during initial assembly) that then closes around the cable to maintain concentricity. In cases where the cable terminus can be swaged on after the cable has been passed through the links it is possible to keep the lumen sufficiently small to eliminate the need for a grommet or similar insert.

Another design feature is related to the surface finish and material type, each of which can affect the friction coefficient between the mating links 230. It is desirable to achieve a relatively high coefficient of friction between the mating links 230 to increase the load holding capacity of the flexible arm 22. It can be advantageous to achieve a friction coefficient greater than 1.0. In this regard it may be desirable to form the convex surface 233 of each link 230 with a granular or otherwise defined matte surface finish to boost the friction coefficient.

The combination of the high modulus of elasticity material used for the links 230, high coefficient of friction between the mating links 230 (e.g., increased by controlled and uniform injection-molded surface finish), as well as the above-described optimum geometry of the links 230, has enabled the load carrying capacity of the above-described configuration to be substantially greater than many prior art stabilizers. Specifically, once the arm 22 is locked, the table mounted stabilizer system has a minimum load carrying capability of 2 ft-lbs torsionally, 25 pounds axially and 10 pounds laterally for rigid, reliable and secure support of an instrument.

The axial passage 234 through the tubular member 236 of each link 230 passes the cable 240, and a control wire to the button 222, and (optionally) provides a passage for the delivery of negative air pressure (vacuum) for suction instruments. The end adapter 210 includes a square insert 212 backed by a flange 212 at one end for insertion into a square tubular receptacle in the base 65. Another ball-and-socket link identical to 230 protrudes integrally from the other side of flange 212, albeit no inner tubular member 236 is required. The hand piece 60 typically allows rotation via connector collar 224 (see FIG. 5) and adapter 220 typically allows hemispherical pivoting of the instrument 70 wielded thereby. The ergonomic hand piece 60 is a contoured member having the arm control button 222 mounted there atop. The throw of actuator 64 is controlled by the button 222 on the instrument-supporting hand piece 60. The hand piece 60 includes an open-ended receptacle for insertion of one of a variety of adapters 220 that will interface with and support a variety of desired surgical tools. The adapter 220 typically allows snap-fit insertion of a vaginal probe 70 or other device. A bayonet type connection (or similar twist locking style of connection) is also a suitable alternative.

The actuator 64 can be a variety of different types. For example, the actuator 64 may be an electronic motor that selectively winds/unwinds a tensioning cable onto a pulley. Alternatively, the actuator 64 may be a linear actuator, or pneumatic cylinder (e.g., air cylinder), hydraulic cylinder, or any other suitable actuator capable of tightening/loosening a cable. The actuator 64 provides the motive force and incorporates control circuitry in actuator housing 54 to selectively tighten/loosen the internal tensioning cable 240 which extends through actuator housing 54 to the flexible arm 22 mounted there atop. Typically, actuator 64 includes an internal actuator control system constructed according to the type of actuation, and generically including one or more position or load sensors, a PLC controller, and hydraulic/pneumatic valves as necessary. By way of example, Duff-Norton™ sells a TracMaster™ line of linear actuators in a variety of stroke lengths, along with accessory control packages and digital position and load indicators that will suffice.

Figure 8:
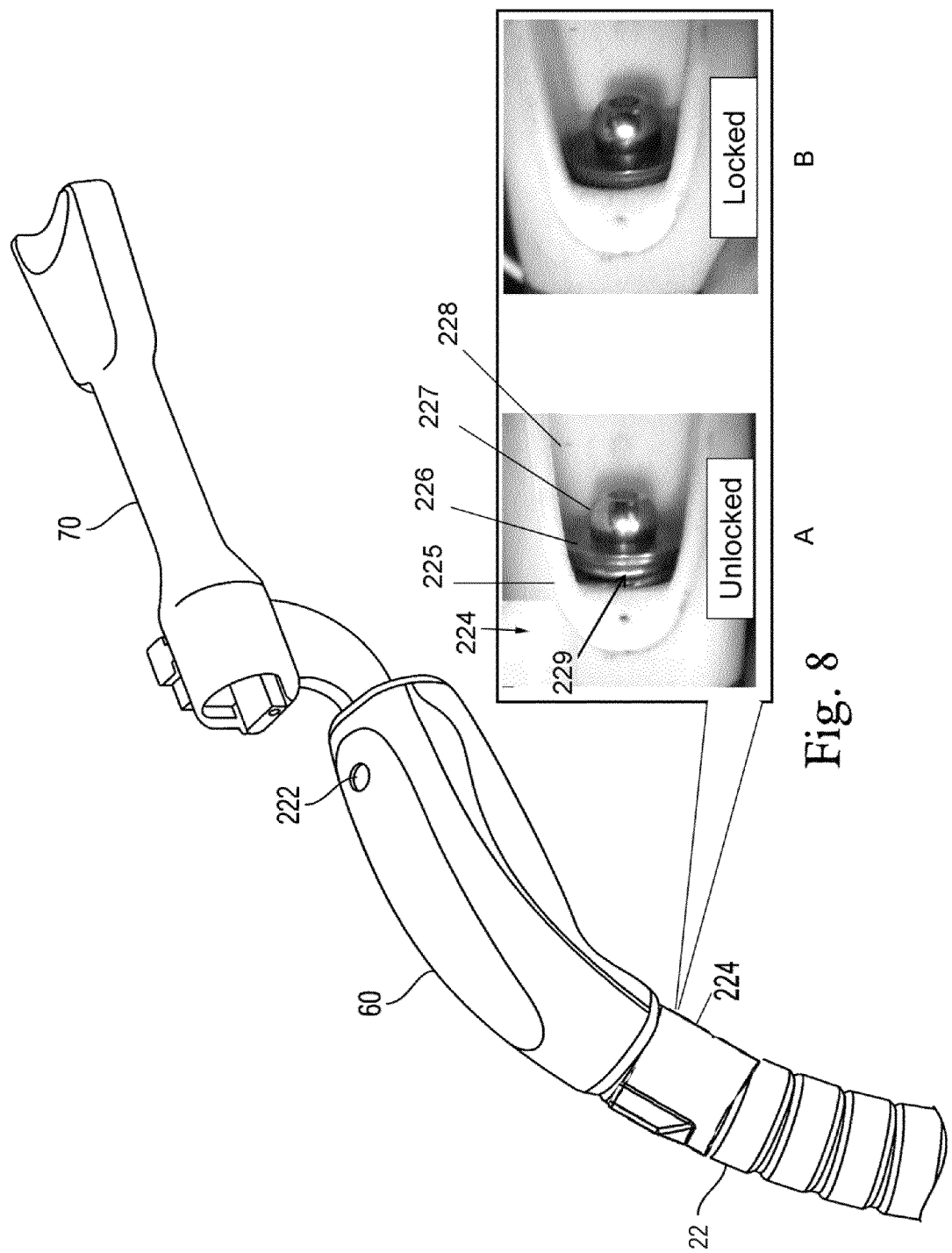
FIG. 8 is an enlarged side-view of a hand piece, that is carrying a vaginal probe and is supported by the flexible arm of the stabilizer systems of FIGS. 1-3.

FIG. 8 is an enlarged side-view of the flexible arm 20 supporting the hand piece 60, which is in turn carrying a vaginal probe 70. The probe-adapter inserts 220 may assume various internal configurations as needed for snap-fit insertion or bayonet locking and secure holding of any of a variety of surgical tools (such as vaginal probe 70, or surgical tools, cutting instruments, cameras or the like). This effectively makes the table mounted stabilizer system 1 universally capable of holding most any instrument, universally capable of manipulating that instrument into any desired position and angle, and then locking it in fixed position. In many cases, the manipulation and locking of the instrument can be carried out with a single hand (or optional voice activated control) by a surgeon or surgical assistant.

One additional feature of the arm 22 helps to minimize or eliminate hand piece shifting or drift, and improve the stability of the probe 70 being supported thereby. The entire flexible neck 22 is tensioned by a preload tensioning mechanism at the hand piece 60. Applicants have found that as small as a 0.0001" gap between adjacent links 230 can cause the cable to kick and/or and start rubbing. The preload tensioning mechanism eliminates gaps between the links 230 and the end supports, which reduces tool drift (motion) during cable 240 actuation. The preload tensioning mechanism is shown in the inset of FIG. 8 and is incorporated into the cable 240 terminus in collar 224. The tensioning cable 240 continues down throughout the arm 22, base 65 and actuator housing 54 and connects to actuator 64, the actuator 64 controlling the tension load on the cable 240. The collar 224 is defined by an interior chamber 228 at the probe 70 end, and a metallic anchor 227 is seated inside the chamber 228. The cable 240 passes into the collar 224 through the anchor 227 and (typically the cable's swage fitting) is anchored thereto on the other side. The anchor 227 is allowed a limited amount of axial float, e.g., a degree of freedom to slide along its axis, and the preload tensioning mechanism imparts a pre-bias to the cable vis-à-vis the anchor 227. This is accomplished by forming the anchor 227 as a cylindrical stem leading to a bulbous head. A washer 226 is fitted to the stem and abuts the head, and a compression spring 229 is mounted on the anchor 227 stem between the head and interior wall of collar 224.

When no tension is applied to the cable 240 by the actuator 64 any cable extension within collar 224 is absorbed by the floating anchor 227 and compression spring 229, which effectively maintains a predetermined pre-bias on the next adjacent link 230 despite unlocking of the flexible arm 22 as seen in the FIG. 8 inset at (A). Conversely, when tension is applied to the cable 240 by the actuator 64 the cable retraction within collar 224 overcomes the compression spring 229, which becomes inoperative as seen in the FIG. 8 inset at (B). Again, as the cable 240 tension is increased the links 230 endure a corresponding increase in compressive load between each mating ball and socket. With the tensioning mechanism, when the cable 240 tension is released the links 230 will relax to a predetermined minimum compressive load between each mating ball and socket, imparted by compression spring 229. This again helps to minimize or eliminate hand piece shifting or drift, and improve the stability of the probe 70 being supported thereby.

One skilled in the art should now understand that the foregoing allows full adjustability of the location of the desired instrument up and down along a vertical axis, forward and back, i.e, toward or away from the patient, and rotationally so that the desired instrument can be angled up or down and side to side. Once locked the table mounted stabilizer system has a minimum load carrying capability of 2 ft-lbs torsionally, 25 pounds axially and 10 pounds laterally for rigid, reliable and secure support of any device.

Other embodiments are within the scope of the following claims.

We claim:

1. A surgical instrument stabilizer system comprising:
an articulating boom that is releasably connectable to a surgical table side rail, the articulating boom comprising
an actuator,
a multi-directional flexible arm having a first end region attached to the actuator, and
a cable extending through the flexible arm, the cable having one end region connected to the actuator and another end region connected to a preload tensioning mechanism, the preload tensioning mechanism comprising a compression spring mounted on an anchor that is attached to the cable, the actuator being operable to tighten and loosen the cable, and the preload tensioning mechanism maintaining an amount of tension in the cable when the actuator loosens the cable; and
a surgical instrument-supporting member attached to a second end region of the flexible arm, the surgical instrument being configured to releasably retain a surgical instrument.

2. The surgical instrument stabilizer system according to claim 1, wherein the flexible arm comprises a plurality of nesting links, each of the nesting links having a hemispherical end region and a concave end region, wherein the hemispherical end regions of the nesting links matingly engage the concave end regions of adjacent nesting links such that the nesting links are movable relative to one another.

3. The surgical instrument stabilizer system according to claim 2, wherein a maximum diameter of the concave end region of one of the nesting links is smaller than a maximum outer diameter of the hemispherical end region of another one of the nesting links that is mated with the concave end region of the one of the nesting links.

4. The surgical instrument stabilizer system according to claim 2, wherein average diameters of the nesting links progressively decrease in the direction of the surgical instrument-supporting member.

5. The surgical instrument stabilizer system according to claim 2, wherein each of the plurality of nesting links has an internal tubular member and an outer wall that concentrically surrounds the internal tubular member, the internal tubular member of each of the nesting links defining a lumen for passage of the cable.

6. The surgical instrument stabilizer system according to claim 5, wherein the outer wall defines the concave end region in each of the nesting links.

7. The surgical instrument stabilizer system according to claim 5, wherein the internal tubular member of each of the nesting links extends axially beyond the outer wall.

8. The surgical instrument stabilizer system according to claim 5, wherein the internal tubular member of each of the nesting links has a bottleneck configuration.

9. The surgical instrument stabilizer system according to claim 5, wherein a first portion of the lumen extending along the concave end region of each of the nesting links has a smaller diameter than a second portion of the lumen extending along the hemispherical end region of each of the nesting links.

10. The surgical instrument stabilizer system according to claim 9, wherein the second portion of the lumen of each of the nesting links receives therein a portion of the tubular member of an adjacent one of the nesting links.

11. The surgical instrument stabilizer system according to claim 10, wherein the lumen and the tubular member of each of the nesting links are configured such that contact between the inner and outer walls, respectively, of adjacent nesting links limits rotations of the adjacent nesting links relative to one another.

12. The surgical instrument stabilizer system according to claim 11, wherein a contact angle at which a compressive force of one of the nesting links contacts an adjacent one of the nesting links is 18-30 degrees.

13. The surgical instrument stabilizer system according to claim 5, wherein the lumen of each of the nesting links has a first end, a central region, and a second end, and the lumen decreases in diameter from the first end to the central region and increases in diameter from the central region to the second end.

14. The surgical instrument stabilizer system according to claim 5, wherein the internal members of the nesting links are shaped to maintain the cable centered within each of the nesting links when the flexible arm is bent into a non-linear configuration.

15. The surgical instrument stabilizer system according to claim 1, wherein the anchor comprises a bulbous head, and the compression spring is mounted between the bulbous head of the anchor and a surface of the surgical instrument-supporting member.

16. The surgical instrument stabilizer system according to claim 15, wherein the compression spring is biased to move the anchor and the cable away from the surface of the surgical instrument-supporting member.

17. The surgical instrument stabilizer system according to claim 16, wherein the surgical instrument-supporting member comprises a collar, and the surface of the surgical instrument-supporting member is an internal surface of the collar.

18. The surgical instrument stabilizer system according to claim 17, wherein the collar is configured to permit rotation of the surgical instrument-supporting member relative to the flexible arm.

19. The surgical instrument stabilizer system according to claim 1, further comprising a rigid arm assembly that supports the articulating boom and that is attached to a side rail of a surgical table by a clamping assembly in a manner such that the rigid arm assembly and the articulating boom can be slid along the side rail.

20. The surgical instrument stabilizer system according to claim 19, further comprising a locking ball coupling that connects the rigid arm assembly to the articulating boom, wherein the locking ball coupling carries the articulating boom at the center of gravity of the articulating boom.

21. The surgical instrument stabilizer system according to claim 1, further comprising a surgical instrument that is secured in the instrument-supporting member and can be repositioned and locked in a desired position and orientation single-handedly.

* * * * *

UNITED STATES PATENT AND TRADEMARK OFFICE
CERTIFICATE OF CORRECTION

| | | |
|---|---|---|
| PATENT NO. | : 8,840,077 B2 | Page 1 of 1 |
| APPLICATION NO. | : 13/589439 | |
| DATED | : September 23, 2014 | |
| INVENTOR(S) | : Walter von Pechmann et al. | |

It is certified that error appears in the above-identified patent and that said Letters Patent is hereby corrected as shown below:

On the Title Page item (56)

Page 2

Column 2 (Other Publications), Line 1, delete "Syustem," and insert -- System, --

Column 2 (Other Publications), Line 4, delete "Sunthetic" and insert -- Synthetic --

Column 2 (Other Publications), Line 8, delete "Bookwaltre" and insert -- Bookwalter --

In the Claims

Column 13

Lines 25-26, delete "instrument" and insert -- instrument-supporting member --

Signed and Sealed this
Twenty-third Day of December, 2014

Michelle K. Lee
*Deputy Director of the United States Patent and Trademark Office*